(12) United States Patent
Wang et al.

(10) Patent No.: US 11,124,763 B2
(45) Date of Patent: Sep. 21, 2021

(54) SYSTEMS AND METHODS FOR GROWING CELL CULTURES

(71) Applicant: Georgia Tech Research Corporation, Atlanta, GA (US)

(72) Inventors: Kan Wang, Atlanta, GA (US); Ben Wang, Atlanta, GA (US); Chun Zhang, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 348 days.

(21) Appl. No.: 16/173,725

(22) Filed: Oct. 29, 2018

(65) Prior Publication Data

US 2019/0127683 A1      May 2, 2019

Related U.S. Application Data

(60) Provisional application No. 62/577,802, filed on Oct. 27, 2017.

(51) Int. Cl.
| | |
|---|---|
| *C12M 3/00* | (2006.01) |
| *C12M 1/00* | (2006.01) |
| *C12N 5/00* | (2006.01) |
| *C12M 1/12* | (2006.01) |
| *B01L 3/00* | (2006.01) |

(52) U.S. Cl.
CPC ............ *C12N 5/0062* (2013.01); *B01L 3/567* (2013.01); *C12M 23/26* (2013.01); *C12M 25/14* (2013.01); *C12N 5/0068* (2013.01); *B01L 2400/06* (2013.01); *C12M 3/00* (2013.01); *C12M 23/20* (2013.01); *C12N 2501/11* (2013.01); *C12N 2501/115* (2013.01); *C12N 2513/00* (2013.01); *C12N 2521/00* (2013.01); *C12N 2533/54* (2013.01)

(58) Field of Classification Search
CPC .............................. C12M 35/02; C12M 35/04
See application file for complete search history.

(56) References Cited

U.S. PATENT DOCUMENTS

| | | | | |
|---|---|---|---|---|
| 2004/0014205 A1* | 1/2004 | Banes | ..................... | C12M 25/14 435/325 |
| 2004/0235153 A1* | 11/2004 | Takagi | .................. | C12M 35/04 435/293.2 |

(Continued)

*Primary Examiner* — Nathan A Bowers
(74) *Attorney, Agent, or Firm* — Troutman Pepper Hamilton Sanders LLP; Ryan A. Schneider; Dustin B. Weeks (57) ABSTRACT

Systems and methods for culturing cells are disclosed. A system can comprise an auxetic scaffold substrate. The substrate can comprise scaffold units at least a portion of which comprise living cells. Scaffold units can be configured to transition between a contracted state and an expanded state. Units can comprise an interior void having a contracted volume in the contracted state and an expanded volume in the expanded state, in which the expanded volume is greater than the contracted volume. Units can be configured to pass a fluid into the interior void of the corresponding unit when the unit transitions from the contracted state to the expanded state. Units can be configured to pass the fluid out of the interior void of the corresponding unit when the unit transitions from the expanded state to the contracted state.

19 Claims, 8 Drawing Sheets

(56) References Cited

U.S. PATENT DOCUMENTS

| | | | |
|---|---|---|---|
| 2007/0213838 A1* | 9/2007 | Hengelmolen | A61F 2/915 623/23.71 |
| 2011/0159522 A1* | 6/2011 | Kamm | G01N 33/5082 435/7.21 |
| 2013/0344601 A1* | 12/2013 | Soman | A61L 27/40 435/396 |
| 2016/0056474 A1* | 2/2016 | Greer | G03F 7/2053 428/221 |
| 2017/0231790 A1* | 8/2017 | Abunassar | A61F 2/844 623/1.11 |

* cited by examiner

SYSTEMS AND METHODS FOR GROWING CELL CULTURES

CROSS REFERENCE TO RELATED APPLICATIONS

This Application claims priority to U.S. Provisional Patent Application No. 62/577,802, filed 27 Oct. 2017, which is hereby incorporated by reference herein in its entirety as if fully set forth below.

FIELD OF THE DISCLOSURE

Embodiments of the present disclosure relate generally to systems and methods for culturing living cells.

BACKGROUND

Bioprinting is considered one of the most effective and promising tools for tissue engineering. Printed tissues and organs have been demonstrated in the past decade. It is widely believed that bioprinting provides solutions to many challenging issues in biomedical research and practice, such as the limited source of donors, the repetitive and unreliable method of using animal models for drug testing, and allogeneic transplant rejection. To date, bioprinting is still confined to laboratory scale fabrications in a limited number of research institutes. An industry-level manufacturing protocol and complete supply chain must be established before the potential of bioprinting can be fully realized. This is a necessity before benefits to a larger population of patients in need can be realized.

Scaling-up bioprinting faces the same major hurdles that general cell manufacturing does. This includes products having a large intrinsic variability, and products having a long lead time. Recent research results in cell manufacturing have revealed the fact that local microenvironment, such as local cell density and the mass exchange rate amongst cells, is a key factor for cell growth rate and cell-to-cell variation. Based on this discovery, the time of cell growth in a bioreactor can be shortened and the variability of the printed tissue can be reduced by controlling the microenvironment.

What is needed, therefore, is a system that considers the cell density and growth rate to regulate the microenvironment during the culture process to improve growth time and improve quality of grown tissue. Embodiments of the present disclosure address these concerns as well as other needs that will become apparent upon reading the description below in conjunction with the drawings.

SUMMARY

Briefly described, embodiments of the present disclosure relate generally to cell culture and growth systems and methods, and processes of using cell culture and growth systems, and, more particularly, to such systems, methods and processes for improved culturing of cell aggregates.

In an exemplary embodiment of the present invention, a system for growing a cell culture comprises an auxetic scaffold substrate comprising scaffold units, at least a portion of the scaffold units comprising living cells, an interior void having a contracted volume and an expanded volume, and configured to transition between a contracted state and an expanded state, the interior void having the contracted volume in the contracted state and the expanded volume in the expanded state, the expanded volume being greater than the contracted volume, wherein each of the at least a portion of the scaffold units is configured to receive a portion of a fluid into the interior void when the unit transitions from the contracted state to the expanded state, and expel a portion of the fluid from the interior void when the unit transitions from the expanded state to the contracted state.

The at least a portion of the scaffold units can comprise all of the scaffold units of the auxetic scaffold substrate.

The portion of the fluid received by a scaffold unit can be substantially the same as the portion of the fluid expelled by the scaffold unit.

A scaffold unit can comprise a fluid inlet configured to enable the scaffold unit to receive the portion of a fluid into the interior void and a fluid outlet configured to enable the scaffold unit to expel the portion of a fluid from the interior void.

The fluid inlets and the fluid outlets can comprise a one-directional valve.

The auxetic scaffold substrate can comprises a cell-laden hydrogel.

The cell-laden hydrogel can comprise mammalian stem cells.

The system can further comprise a growth factor solution coated upon at least a portion of the auxetic scaffold substrate.

The growth factor solution can include one or more of collagen, basic fibroblast growth factor, and epidermal growth factor.

The fluid can include one or more of amino acids, salts, sugars, and vitamins.

The system can further comprise a first member coupled to a first side of the auxetic scaffold substrate, and a second member coupled to a second side of the auxetic scaffold substrate, wherein the second member is configured to move between a contracted position and an expanded position, wherein each of the at least a portion of the scaffold units is in the contracted state when the second member is in the contracted position, and wherein each of the at least a portion of the scaffold units is in the expanded state when the second member is in the expanded position.

The system can further comprise a controller configured to cycle the second member between the contracted position and the expanded position.

The controller can be further configured to, based on a parameter associated with the auxetic scaffold substrate, adjust at least one of at least one of the contracted position and the expanded position of the second member and a frequency at which the location of the second member is cycled between the contracted position and the expanded position.

The parameter can be indicative of at least one of a current cell-density of the living cells and a current growth rate of the living cells.

The auxetic scaffold substrate can be a multi-layered and manufactured using a three-dimensional bioplotter.

In an exemplary embodiment of the present invention, a method of facilitating cell growth comprises providing living cells in units of scaffold substrate, wherein at least a portion of the units of scaffold substrate each comprise an interior void having a contracted volume and an expanded volume and a unit construction that is configured to transition between a contracted state and an expanded state, the interior void having the contracted volume in the contracted state and the expanded volume in the expanded state, the expanded volume being greater than the contracted volume, and providing the living cells with a fluid comprising one or more materials selected from the group consisting of amino acids, salts, sugars, and vitamins, wherein the unit construction of each of the at least a portion of the units of scaffold substrate is further configured to receive a portion of the fluid into the interior void when the unit transitions from the contracted state to the expanded state, and expel a portion of the fluid from the interior void when the unit transitions from the expanded state to the contracted state.

The scaffold substrate of the method can comprise an auxetic scaffold substrate providing the unit construction enabling the transition between the contracted state and the expanded state.

The at least a portion of the units of scaffold substrate of the method can comprise all of the units of scaffold substrate, wherein the portion of the fluid received by a scaffold unit can be substantially the same as the portion of the fluid expelled by the scaffold unit.

The method can further comprise moving a second member coupled to a second side of the scaffold substrate between a contracted position and an expanded position, wherein a first member is coupled to a first side of the auxetic scaffold substrate, wherein each of the at least a portion of the units of scaffold substrate is in the contracted state when the second member is in the contracted position, and wherein each of the at least a portion of the units of scaffold substrate is in the expanded state when the second member is in the expanded position.

The method can further comprise moving the second member at a first frequency adjustable based on a parameter associated with the auxetic scaffold substrate.

The parameter can be indicative of at least one of a current cell-density of the living cells and a current growth rate of the living cells.

According to another aspect of the present invention, a system for growing a cell culture is provided. The system can comprise a dynamic scaffold substrate. The dynamic scaffold substrate can further comprise adaptive technologies that are self-regulated for near or full automated, real-time adjustments. The dynamic scaffold in an exemplary embodiment comprises an auxetic scaffold substrate.

The auxetic scaffold substrate can comprise scaffold units. A scaffold unit can comprise living cells. Scaffold units can be configured to transition (discretely or distinctly) between a contracted state and an expanded state. The units can comprise an interior void having a contracted volume in the contracted state and an expanded volume in the expanded state. The expanded volume can be greater than the contracted volume. The units can be configured to pass a fluid into the interior void of the corresponding unit when the unit transitions from the contracted state to the expanded state. The units can be configured to pass the fluid out of the interior void of the corresponding unit when the unit transitions from the expanded state to the contracted state.

In any of the embodiments described herein, the scaffold units can comprise a fluid inlet and a fluid outlet. The fluid inlet can be configured to pass a fluid into the interior void of the corresponding unit when the unit transitions from the contracted state to the expanded state. The fluid outlet can be configured to pass the fluid out of the interior void of the corresponding unit when the unit transitions from the expanded state to the contracted state.

In any of the embodiments described herein, the fluid inlet and fluid outlet of the scaffold units can comprise a one-directional valve. The one-directional valve on the inlet can be configured to permit the fluid to flow through the fluid inlet and into the interior void when the corresponding unit transitions from the contracted state to the expanded state. The one-directional valve on the outlet can be configured to permit the fluid to flow through the fluid outlet and out of the interior void when the corresponding unit transitions from the expanded state to the contracted state. The one-directional valves may be further configured to prevent the fluid from flowing through the fluid outlet and out of the interior void when the corresponding unit transitions from the expanded state to the contracted state, and through the fluid inlet and into the interior void when the corresponding unit transitions from the contracted state to the expanded state.

In any of the embodiments described herein, the auxetic scaffold substrate can comprise a cell-laden hydrogel.

In any of the embodiments described herein, the cell-laden hydrogel can comprise mammalian stem cells.

In any of the embodiments described herein, the auxetic scaffold substrate can be coated with a growth factor solution.

In any of the embodiments described herein, the growth factor solution can be selected from a group of collagen, basic fibroblast growth factor, and epidermal growth factor.

In any of the embodiments described herein, the fluid can comprise one or more materials selected from a group consisting of amino acids, salts, sugars, and vitamins.

In any of the embodiments described herein, a first member can be coupled to a first side of the auxetic scaffold substrate, and a second member can be coupled to a second side of the auxetic scaffold substrate. The second member can be movable between a contracted position and an expanded position. Scaffold units can be in the contracted state when the second member is in the contracted position. Scaffold units can be in the expanded state when the second member is in the expanded position.

In any of the embodiments described herein, the invention can comprise a controller configured to cycle a location of the second member between the contracted position and the expanded position.

In any of the embodiments described herein, the controller can be further configured to adjust at least one of the contracted position and the expanded position of the second member. The controller can be further configured to adjust a frequency at which the location of the second member is cycled between the contracted position and the expanded position. The controller can be configured to make at least one of the aforementioned adjustments based on a parameter associated with the auxetic scaffold substrate.

In any of the embodiments described herein, the parameter could be indicative of at least one of a current cell-density of the cells, and a current growth rate of the living cells.

In any of the embodiments described herein, the auxetic scaffold substrate can be multi-layered and could be manufactured using a three-dimensional bioplotter.

According to another aspect of the present invention, a method of facilitating cell growth is provided. The method can comprise forming an auxetic scaffold substrate. The auxetic scaffold substrate can comprise scaffold units. The scaffold units can comprise living cells. The scaffold units can be configured to transition between a contracted state and an expanded state. The units can comprise an interior void having a contracted volume in the contracted state and an expanded volume in the expanded state. The expanded volume can be greater than the contracted volume. Units can be configured to pass a fluid into the interior void of the corresponding unit when the unit transitions from the contracted state to the expanded state. The units can be configured to pass the fluid out of the interior void of the corresponding unit when the unit transitions from the expanded state to the contracted state. The auxetic scaffold substrate can be expanded such that scaffold units are in the expanded state. The auxetic scaffold substrate can be contracted such that scaffold units are in the contracted state.

In any of the embodiments described herein, expanding the auxetic scaffold substrate can increase a volume of fluid in the interior voids of scaffold units. Contracting the auxetic scaffold substrate can decrease the volume of fluid in the interior voids of scaffold units.

In any of the embodiments described herein, a first member can be coupled to a first side of the auxetic scaffold substrate, and a second member can be coupled to a second side of the auxetic scaffold substrate. The second member can be movable between a contracted position in which scaffold units are in the contracted state, and an expanded position in which scaffold units are in the expanded state. Expanding the auxetic scaffold structure can comprise moving the second member from the contracted position to the expanded position. Contracting the auxetic scaffold structure can comprise moving the second member from the expanded position to the contracted position.

In any of the embodiments described herein, the expanding and contracting steps can be cycled at a first frequency. The first frequency can be adjusted based on a parameter associated with the auxetic scaffold substrate.

In any of the embodiments described herein, the parameter can be indicative of at least one of a current cell density of living cells, and a current growth rate of living cells.

In any of the embodiments described herein, at least one of the contracted position and the expanded position can be adjusted based on a parameter associated with the auxetic scaffold substrate.

In any of the embodiments described herein, the parameter can be indicative of at least one of a current cell density of living cells, and a current growth rate of living cells.

In an exemplary embodiment of the present invention, a system for growing a cell culture comprises an auxetic scaffold comprising a plurality of living cells. The growth rate and/or survival rate of the plurality of living cells is greater in the system than in conventional systems employing non-auxetic scaffolds.

In some embodiments of the present invention, the number of living cells in an inventive system employing an auxetic scaffold after a predetermined period of time is 5% greater than the number of living cells in a conventional system employing a non-auxetic scaffold after the same predetermined period of time.

In some embodiments of the present invention, the number of living cells in an inventive system employing an auxetic scaffold after a predetermined period of time is 10% greater than the number of living cells in a conventional system employing a non-auxetic scaffold after the same predetermined period of time.

In some embodiments of the present invention, the number of living cells in an inventive system employing an auxetic scaffold after a predetermined period of time is 15% greater than the number of living cells in a conventional system employing a non-auxetic scaffold after the same predetermined period of time.

In some embodiments of the present invention, the number of living cells in an inventive system employing an auxetic scaffold after a predetermined period of time is 20% greater than the number of living cells in a conventional system employing a non-auxetic scaffold after the same predetermined period of time.

In some embodiments of the present invention, the number of living cells in an inventive system employing an auxetic scaffold after a predetermined period of time is 25% greater than the number of living cells in a conventional system employing a non-auxetic scaffold after the same predetermined period of time.

In some embodiments of the present invention, the number of living cells in an inventive system employing an auxetic scaffold after a predetermined period of time is 30% greater than the number of living cells in a conventional system employing a non-auxetic scaffold after the same predetermined period of time.

In some embodiments of the present invention, the number of living cells in an inventive system employing an auxetic scaffold after a predetermined period of time is 35% greater than the number of living cells in a conventional system employing a non-auxetic scaffold after the same predetermined period of time.

In some embodiments of the present invention, the number of living cells in an inventive system employing an auxetic scaffold after a predetermined period of time is 40% greater than the number of living cells in a conventional system employing a non-auxetic scaffold after the same predetermined period of time.

In some embodiments of the present invention, the number of living cells in an inventive system employing an auxetic scaffold after a predetermined period of time is 45% greater than the number of living cells in a conventional system employing a non-auxetic scaffold after the same predetermined period of time.

In some embodiments of the present invention, the number of living cells in an inventive system employing an auxetic scaffold after a predetermined period of time is 50% greater than the number of living cells in a conventional system employing a non-auxetic scaffold after the same predetermined period of time.

In some embodiments of the present invention, the number of living cells in an inventive system employing an auxetic scaffold after a predetermined period of time is 55% greater than the number of living cells in a conventional system employing a non-auxetic scaffold after the same predetermined period of time.

In some embodiments of the present invention, the number of living cells in an inventive system employing an auxetic scaffold after a predetermined period of time is 60% greater than the number of living cells in a conventional system employing a non-auxetic scaffold after the same predetermined period of time.

In some embodiments of the present invention, the number of living cells in an inventive system employing an auxetic scaffold after a predetermined period of time is 65% greater than the number of living cells in a conventional system employing a non-auxetic scaffold after the same predetermined period of time.

In some embodiments of the present invention, the number of living cells in an inventive system employing an auxetic scaffold after a predetermined period of time is 70% greater than the number of living cells in a conventional system employing a non-auxetic scaffold after the same predetermined period of time.

In some embodiments of the present invention, the number of living cells in an inventive system employing an auxetic scaffold after a predetermined period of time is 75% greater than the number of living cells in a conventional system employing a non-auxetic scaffold after the same predetermined period of time.

In some embodiments of the present invention, the number of living cells in an inventive system employing an auxetic scaffold after a predetermined period of time is 80% greater than the number of living cells in a conventional system employing a non-auxetic scaffold after the same predetermined period of time.

In some embodiments of the present invention, the number of living cells in an inventive system employing an auxetic scaffold after a predetermined period of time is 85% greater than the number of living cells in a conventional system employing a non-auxetic scaffold after the same predetermined period of time.

In some embodiments of the present invention, the number of living cells in an inventive system employing an auxetic scaffold after a predetermined period of time is 90% greater than the number of living cells in a conventional system employing a non-auxetic scaffold after the same predetermined period of time.

In some embodiments of the present invention, the number of living cells in an inventive system employing an auxetic scaffold after a predetermined period of time is 95% greater than the number of living cells in a conventional system employing a non-auxetic scaffold after the same predetermined period of time.

In some embodiments of the present invention, the number of living cells in an inventive system employing an auxetic scaffold after a predetermined period of time is 100% greater than the number of living cells in a conventional system employing a non-auxetic scaffold after the same predetermined period of time.

In some embodiments of the present invention, the number of living cells in an inventive system employing an auxetic scaffold after a predetermined period of time is 125% greater than the number of living cells in a conventional system employing a non-auxetic scaffold after the same predetermined period of time.

In some embodiments of the present invention, the number of living cells in an inventive system employing an auxetic scaffold after a predetermined period of time is 150% greater than the number of living cells in a conventional system employing a non-auxetic scaffold after the same predetermined period of time.

In some embodiments of the present invention, the number of living cells in an inventive system employing an auxetic scaffold after a predetermined period of time is 175% greater than the number of living cells in a conventional system employing a non-auxetic scaffold after the same predetermined period of time.

In some embodiments of the present invention, the number of living cells in an inventive system employing an auxetic scaffold after a predetermined period of time is 200% greater than the number of living cells in a conventional system employing a non-auxetic scaffold after the same predetermined period of time.

In any of the embodiments discussed above, the predetermined period of time can be one one day, three days, seven days, 14 days, 21 days, or 28 days.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE FIGURES

Reference will now be made to the accompanying figures and diagrams, which are not necessarily drawn to scale, and wherein.

DETAILED DESCRIPTION

The present invention provides improved systems and methods for growing a culture of cells and producing high-quality cell tissues. Various embodiments of the present disclosure also make it possible to grow high-quality cell tissues in a shorter lead time than with conventional systems and methods.

To provide such features, some embodiments of the present invention utilize an auxetic material to improve nutrient and waste exchange in the cell culture. Because the material containing the cell culture is dynamic and can be repeatedly expanded and contracted to improve fluid flow around the cell culture, cell culture growth can be closely monitored and regulated. To maximize growth and produce highly specific sets of cells, some embodiments of the present invention provide a system that adjusts the expansion and contraction parameters to finely tune the cell culture's growth process. Utilizing this type of self-regulation of the growth process can produce highly specific and highly viable cultures of cells for targeted tissue, while reducing cell variability and production lead times.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

It should also be noted that, as used in the specification and the appended claims, the singular forms "a," "an" and "the" include plural references unless the context clearly dictates otherwise. References to a composition containing "a" constituent is intended to include other constituents in addition to the one named.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter. Additionally, the components described herein may apply to any other component within the disclosure. Merely discussing a feature or component in relation to one embodiment does not preclude the feature or component from being used or associated with another embodiment.

To facilitate an understanding of the principles and features of the disclosure, various illustrative embodiments are explained below. In particular, the presently disclosed subject matter is described in the context of being a cell culturing device utilizing an auxetic materials for improving fluid circulation during the culturing of cell aggregates. The present disclosure, however, is not so limited and can be applicable in other contexts. For example and not limitation, some embodiments of the present disclosure may utilize other materials, systems, and methods for improving the control of fluid circulation during the culturing of cell aggregates. These embodiments are contemplated within the scope of the present disclosure. Accordingly, when the present disclosure is described in the context of a auxetic materials for culturing cell aggregates, it will be understood that other embodiments can take the place of those referred to.

Figure 1A:
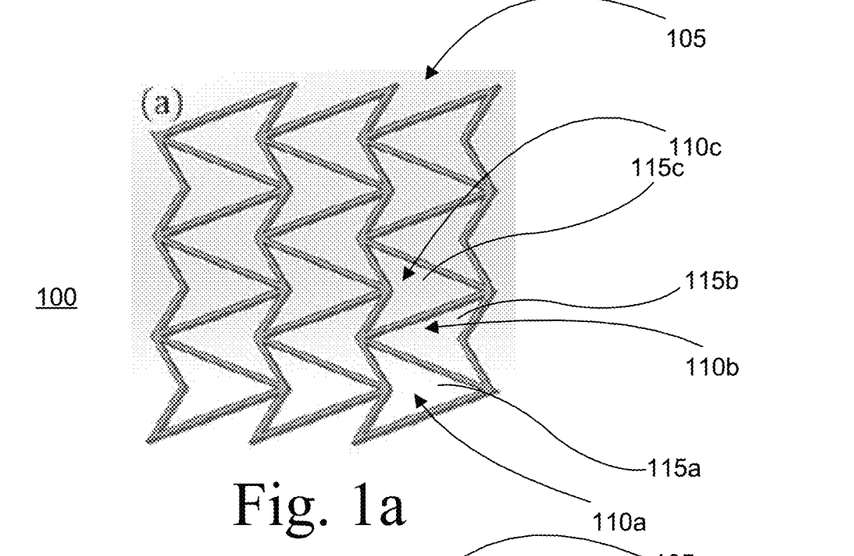
FIG. 1a depicts a system for growing a cell culture, according to an exemplary embodiment of the present invention.
Figure 1B:
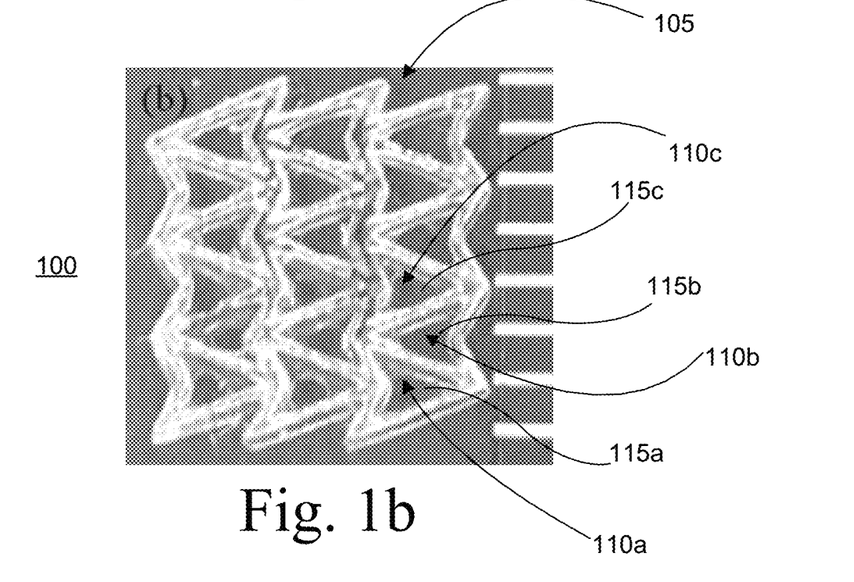
FIG. 1b provides a microscopic image of a system for growing a cell culture, according to an exemplary embodiment of the present invention. Each grid mark on the right side of FIG. 1b represents 1 mm.

As shown in FIGS. 1a-f, an exemplary embodiment of the present invention can provide a system 100 for growing a cell culture. The system 100 can comprise an auxetic scaffold substrate 105. The substrate can comprise scaffold units 110a-c. These units 110a-c can be joined together to form interior voids 115a-c therein. For example, as shown in FIG. 1a, scaffold unit 110a can define interior void 115a. As also shown, a portion of scaffold unit 110a can also form scaffold unit 110b, which defines a second interior void 115b.

The scaffold units 110a-c can be made of many different materials. In some embodiments of the present invention, the scaffold units 110a-c can be made of one or more materials that render the scaffold units 110a-c auxetic. Accordingly, the scaffold units 110a-c can transition between a contracted state and an expanded state. The volume of the interior voids 115a-c can increase as the scaffold units 110a-c transition from the contracted state to the expanded state and can decrease as the scaffold units 110a-c transition from the expanded state to the contracted state. It is contemplated that the various interior voids 115a-c of each of the scaffold units 110a-c can have different interior volumes in both the expanded and contracted state. For example, when in the contracted state, interior void 115a can have a different volume than interior voids 115b and/or 115c. Likewise, when in the expanded state, interior void 115a can have a different volume than interior voids 115b and/or 115c. It is also contemplated that, in some embodiments of the present invention, scaffold units 110a-c can have substantially equal volumes for the interior voids in the expanded and contracted states. For example, when in the contracted state, interior void 115a can have the same volume as interior voids 115b and/or 115c. Likewise, when in the expanded state, interior void 115a can have the same volume as interior voids 115b and/or 115c.

The auxetic scaffold substrate can be disposed in a fluid, such that portions of the fluid are contained within the interior voids 115a-c of the scaffold units 110a-c. Accordingly, when the volume of the interior voids 115a-c increases and decreases as a result of the units cycling between the expanded and contracted states, respectively, the amount of fluid in the interior voids also increases and decreases, respectively. This results in improved fluid flow around the scaffold substrate, which can contain living cells. This improved fluid flow can stimulate cell growth.

Figure 1C:
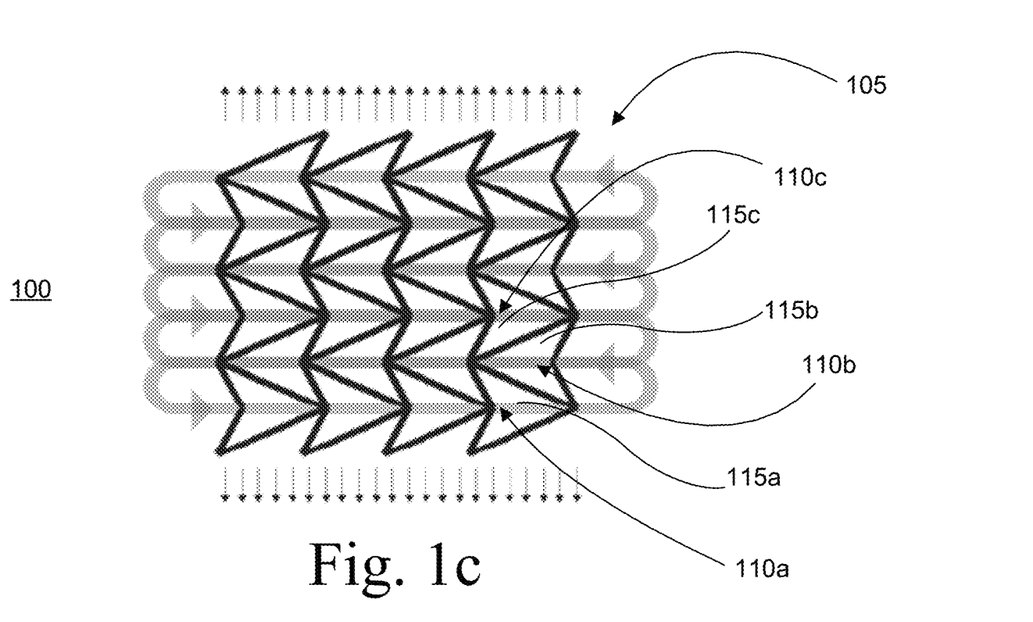
FIG. 1c depicts a system for growing a cell culture with an auxetic scaffold substrate in an expanded state, according to an exemplary embodiment of the present invention.
Figure 1D:
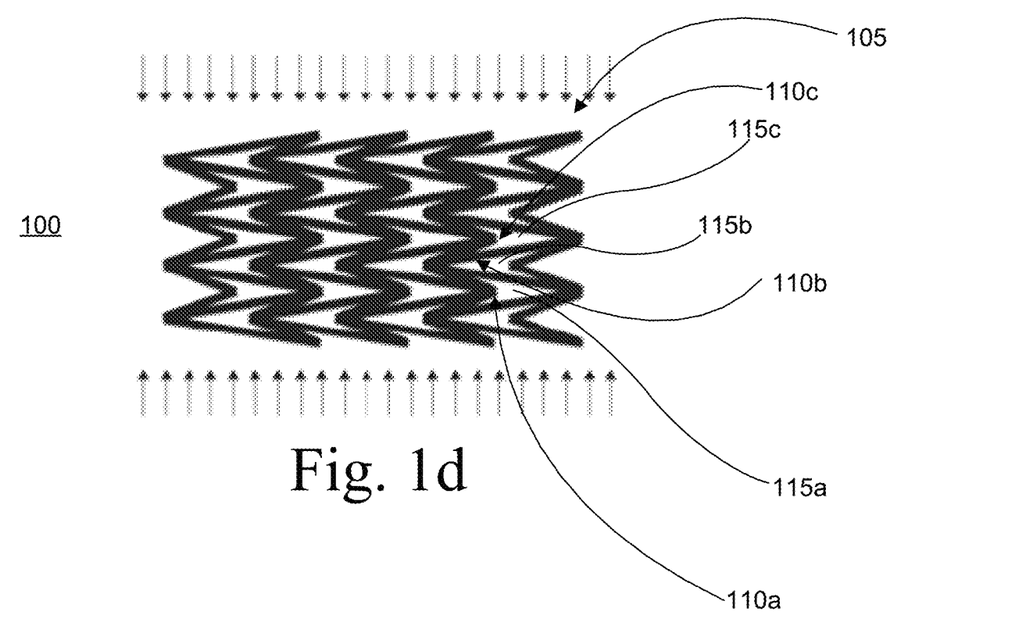
FIG. 1d depicts a system for growing a cell culture with an auxetic scaffold substrate in a contracted state, according to an exemplary embodiment of the present invention.

FIG. 1c illustrates a scaffold substrate 105 in the expanded state, while FIG. 1d illustrates a scaffold substrate in the contracted state. As shown, the volume of the interior voids 115a-c is greater in the expanded state (FIG. 1c) than in the contracted state (FIG. 1d).

The scaffold units 110 can have many different geometrical shapes, in accordance with various embodiments of the present invention. Though the scaffold units 110 shown in FIGS. 1a-f comprise a double arrowhead shape, the invention is not so limited.

Figure 1E:
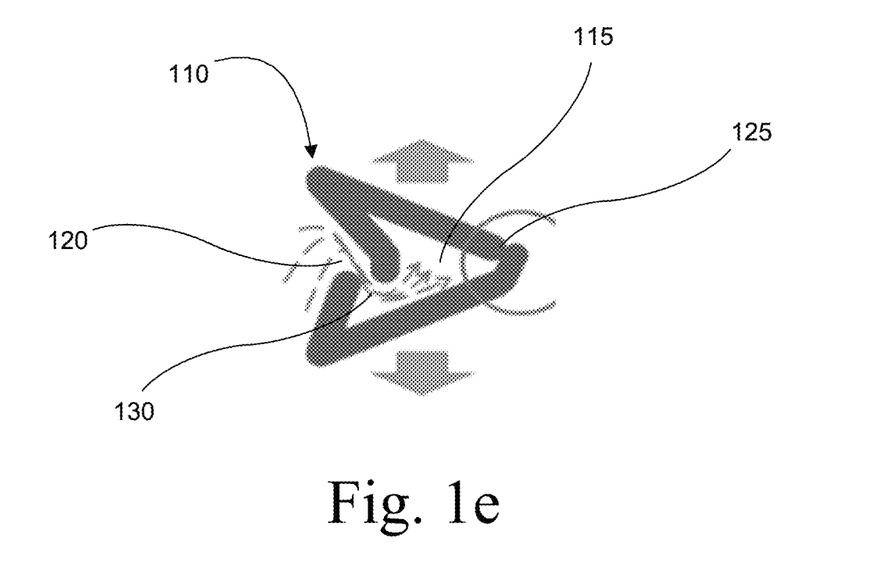
FIG. 1e depicts an auxetic scaffold substrate unit an expanded state, according to an exemplary embodiment of the present invention.

FIG. 1e illustrates a scaffold unit 110 transitioning from a contracted state to an expanded state, which causes the volume of interior void 115 to increase. As the volume increases, fluid 130 enters the interior void 115 through a fluid inlet 120, causing fluid circulation around portions of the scaffold unit 110.

Figure 1F:
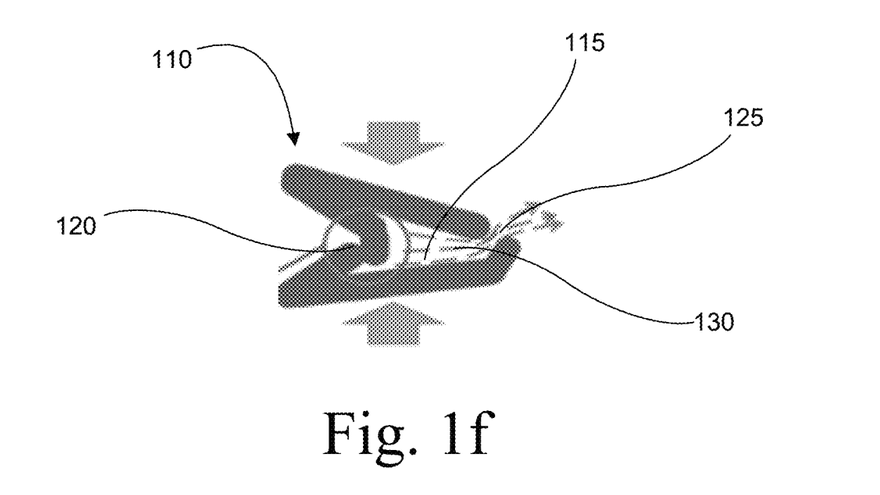
FIG. 1f depicts an auxetic scaffold substrate unit a contracted state, according to an exemplary embodiment of the present invention.

FIG. 1f illustrates a scaffold unit 110 transitioning from the expanded state to the contracted state, which causes the volume of interior void 115 to decrease. As the volume decreases, fluid 130 exits the interior void 115 through a fluid outlet 125, causing additional circulation around portions of the scaffold unit.

As shown in FIGS. 1e-f, the fluid inlet 120 and fluid outlet 125 can comprise one-directional valves to control the flow of fluid into and out of the interior void 115. The one-directional valves can be integral with the scaffold unit 110. For example, fluid inlet 120 can comprise a one-directional valve that permits fluid to flow into the interior void 115 and prevents fluid from flowing out of the interior void 115, when the unit transitions from the contracted state to the expanded state. Similarly, fluid outlet 125 can comprise a one-directional valve that permits fluid to flow out of the interior void 115 and prevents fluid from flowing into the interior void 115, when the unit transitions from the expanded state to the contracted state.

Figure 2A:
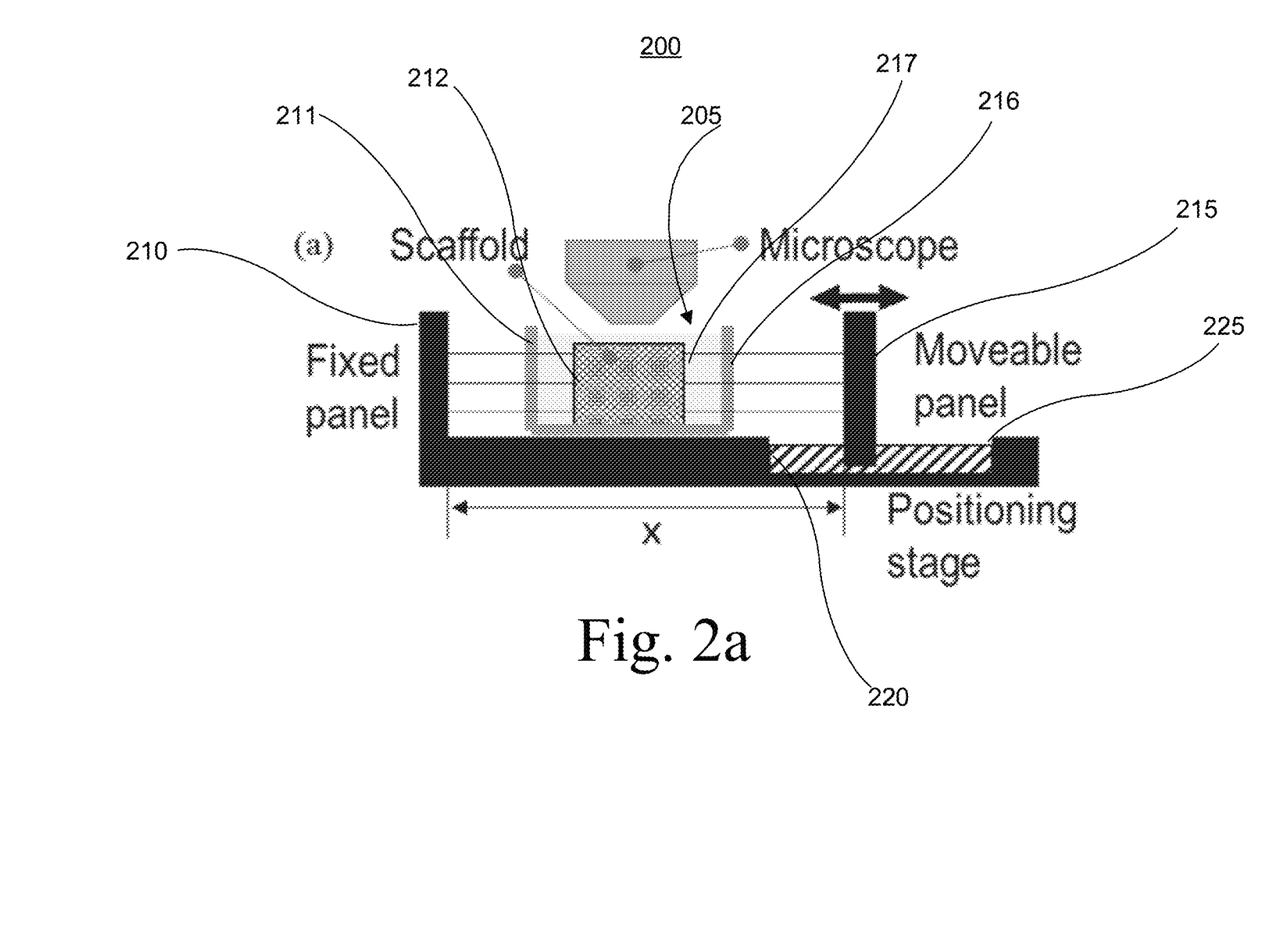
FIG. 2a depicts a system for growing a cell culture, according to an exemplary embodiment of the present invention.

FIG. 2a illustrates a system 200 for facilitating cell growth that permits control over the expansion and contraction of an auxetic scaffold substrate 205, in accordance with an exemplary embodiment of the present invention. The system can comprise a first member 210 coupled to a first side 212 of the scaffold substrate 205 and a second member 215 coupled to a second side 217 of the scaffold substrate. The scaffold substrate can be contained within a volume of fluid defined by walls 211 and 216. In some embodiments of the present invention, at least one of the first member 210 and the second member 215 can be movable, in which movement causes the auxetic scaffold substrate 205 to transition between the contracted and expanded states. As shown in FIG. 2a, the location of the first member 210 can be fixed and the second member 215 can be movable between a contracted position 220 and an expanded position 225. The auxetic scaffold substrate is in the contracted state when the second member 215 is at the contracted position 220 and expands as the second member transitions to the expanded position 225. Accordingly, by altering the location of the expanded position 225, the amount of expansion of the auxetic scaffold substrate 205 can be adjusted.

The system 200 can also include a controller (not shown) configured to alter the location of at least one of the first member 210 and the second member 215. For example, the controller can be configured to cycle the location of the second member 215 between the contracted position 220 and the expanded position 225. The cycling can be periodic. The controller can adjust the frequency of the cycling.

The controller can also be configured to monitor a parameter associated with the system 200. For example, the parameter associated with the system 200 can include, but is not limited to, a fluid temperature, a cell density, a cell growth rate, a concentration of an ingredient in the fluid (e.g., a nutrient or amino acid concentration of the fluid), a flow rate of the fluid, and the like. Based on the parameter, the controller can also be configured to adjust a location of the first member 210 and/or second member 215. For example, in response to the parameter, the controller can adjust the location of the expanded position 225. If the controller adjusts the location of the expanded position 225 such that the expanded position 225 is located further away from the contracted position 220, the auxetic scaffold substrate 205 can further expand. To the contrary, if the controller adjusts the location of the expanded position 225 such that the expanded position 225 is located closer to the contracted position 220, the auxetic scaffold substrate 205 can expand less. Alternatively, or additionally, the controller can adjust the frequency at which the auxetic scaffold substrate 205 is cycled between the expanded and contracted state. For example, the controller can adjust the speed (and thus frequency) at which the second member 215 is cycled between the contracted position 220 and the expanded position 225.

This level of control can be beneficial to adjust cell growth. For example, if the controller determines that cell-growth is lower than desired, the controller might increase the level of expansion of the frequency of expansion and contraction to further stimulate fluid circulation about the scaffold substrate 205. The controller could also seek to ensure a constant cell density is maintained as the cell grows by continually expanding the scaffold over time as additional cells grow.

The systems described herein are particularly useful in the cultivation of living cells. The scaffold substrates can be manufactured to include living cells located therein. For example, the scaffold substrate can comprise a cell-laden hydrogel. The cells can be many different types of living cells, including, but not limited to, mammalian stem cells. During the cultivation process, the cells located in the scaffold substrate may replicate at least in part due to the circulation of fluid around the substrate.

In some embodiments the auxetic scaffold substrate can be coated with a growth factor solution to further stimulate cell growth. The growth factor solution can be many growth factor solutions, including, but not limited to, collagen, basic fibroblast growth factor, and epidermal growth factor.

Various embodiments of the present invention can use many different types of fluids to stimulate cell growth. The fluid can include many different ingredients, including but not limited to, amino acids, salts, sugars, vitamins, and the like.

Figure 5:
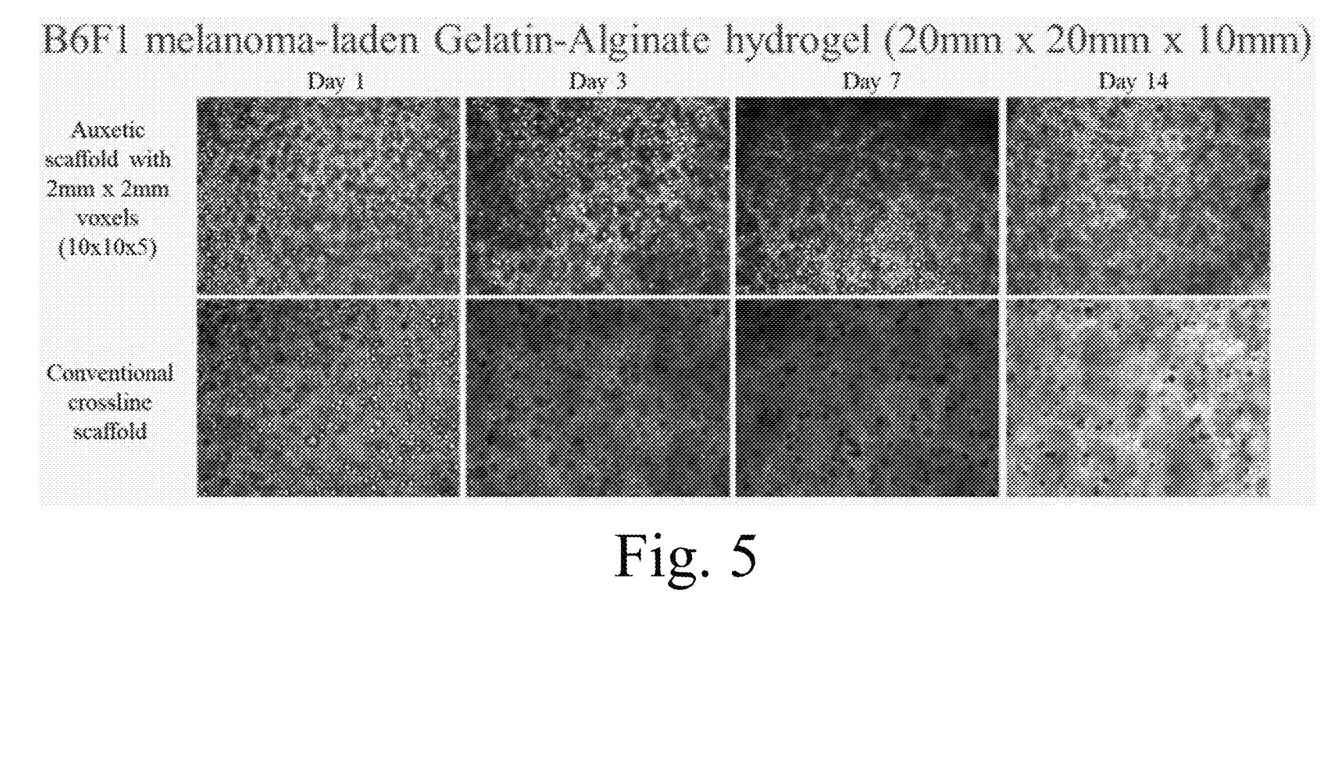
FIG. 5 provides microscopic images of cell-cultures grown using an auxetic scaffold in accordance with an exemplary embodiment of the present invention compared to cell-cultures grown using a conventional system with a non-auxetic scaffold.

FIG. 5 illustrates a method of making the systems described herein, in accordance with some embodiments of the present invention. The method can generally include the steps of: printing supporting walls 505, printing a scaffold layer 510, and removing the supporting walls and crosslinking one or more polymers in the scaffold layer 515, resulting in a freestanding auxetic scaffold 520. In some embodiments, the auxetic scaffold is multi-layered, such that the steps of printing the supporting walls 505 and printing the scaffold layer are repeated for each layer. The printing steps can be performed with a three-dimensional bioplotter.

A more detailed method of manufacturing and using an auxetic scaffold, in accordance with an exemplary embodiment of the present invention, will now be described.

GelMA can be synthesized by the direct reaction of gelatin (10%, type A) with MA (1%) in phosphate buffer (pH 7.4) at 50° C. This reaction introduces methacryloyl substitution groups on the reactive amine and hydroxyl groups of the amino acid residues. Different degrees of methacryloyl substitution can be achieved in gelMA, which produces gelMA with different physical properties. Once the substitution reaction is stopped by diluting the reaction mixture (typically 5×) with phosphate buffer, the resulting solution can then be dialyzed against deionized water through a dialysis tubing for 5-7 days to allow complete removal of the low-molecular-weight impurities, which are potentially cytotoxic. Finally, the dialyzed solution will be freeze dried and stored, preferably under refrigeration, until use.

The freeze-dried gel-MA powder can then be dissolved in PBS at 50° C. for 10 min. The solution can be mixed with hMSC to create multiple levels of cell densities, e.g., three levels at 1.5×105 cells/mL, 1.5×106 cells/mL, and 1.5×107 cells/mL. The cell-laden hydrogels can then be transferred into a syringe and loaded into a bioplotter, e.g., a GESiM bioplotter. The mixed solutions can be degassed for at least 10 min prior to loading with cells. The UV lamp model can be used for the cell-laden hydrogel sample curing (UV-A light, 365 nm, 4 mW/cm$^2$). After optimization, 3 mm thick constructs of 10×10 mm$^2$ can be created with a layer thickness of 150-200 μm and fiber spacing of 350 μm and 550 μm. The bioplotter can be placed in a flow cabinet and constructs can be printed on sterile glass cover slips. After fabricating the cell-laden scaffold, the scaffold can be printed with different growth factor solutions (e.g., collagen, FGF-2, or EGF) using another syringe on the GESiM bioplotter, and the coated scaffold can be dried at room temperature for 1 h. Furthermore, the coated constructs can be cultured at 37° C. and 5% $CO_2$. Each construct can be cultured in a 6-well culture plate. To each well, 4 ml of Dulbecco's modified Eagle medium (DMEM) can be added.

The cell-laden scaffolds can be cultured in DMEM for different days. Cell cultures can be incubated at 37° C. in a 5% $CO_2$ atmosphere. After different culturing times, cell viability will be evaluated using the PrestoBlue® (Invitrogen) assay. The absorbance values can be detected by a multi-well spectrophotometer (Hitachi, Tokyo, Japan) at 570 nm with a reference wavelength of 600 nm.

Figure 2B:
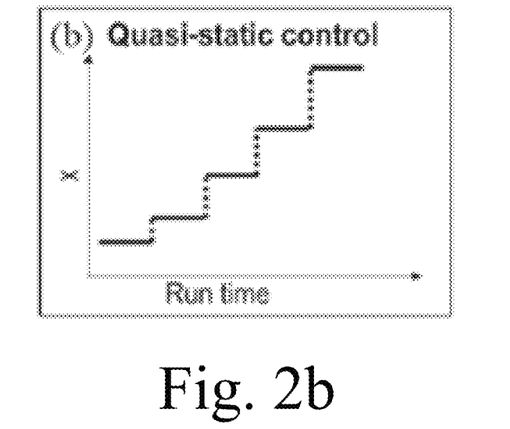
FIG. 2b depicts quasi-static control of the expansion of an auxetic scaffold substrate, according to an exemplary embodiment of the present invention.
Figure 2C:
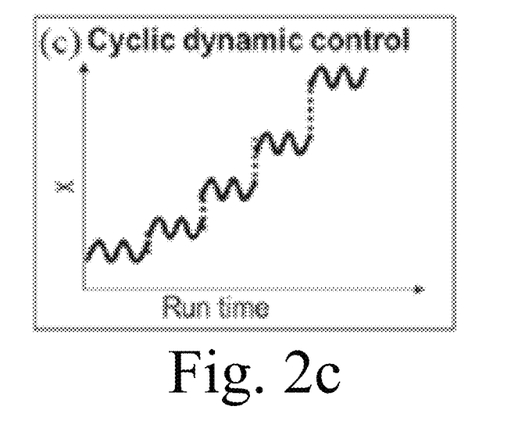
FIG. 2c depicts cyclic dynamic control of the expansion of an auxetic scaffold substrate, according to an exemplary embodiment of the present invention.
Figure 3A:
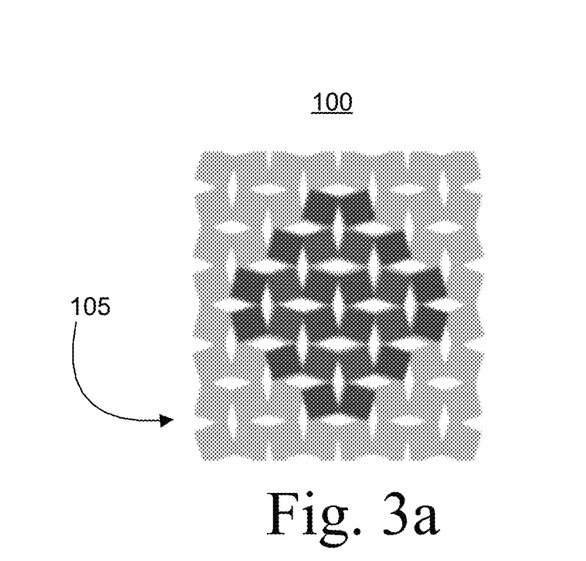
FIG. 3a depicts a system for growing a cell culture with an auxetic scaffold substrate in an expanded state, according to an exemplary embodiment of the present invention.
Figure 3B:
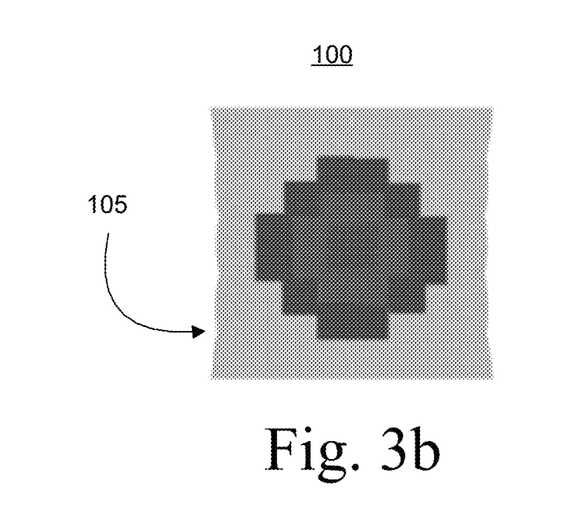
FIG. 3b depicts a system for growing a cell culture with an auxetic scaffold substrate in a contracted state, according to an exemplary embodiment of the present invention.
Figure 4:
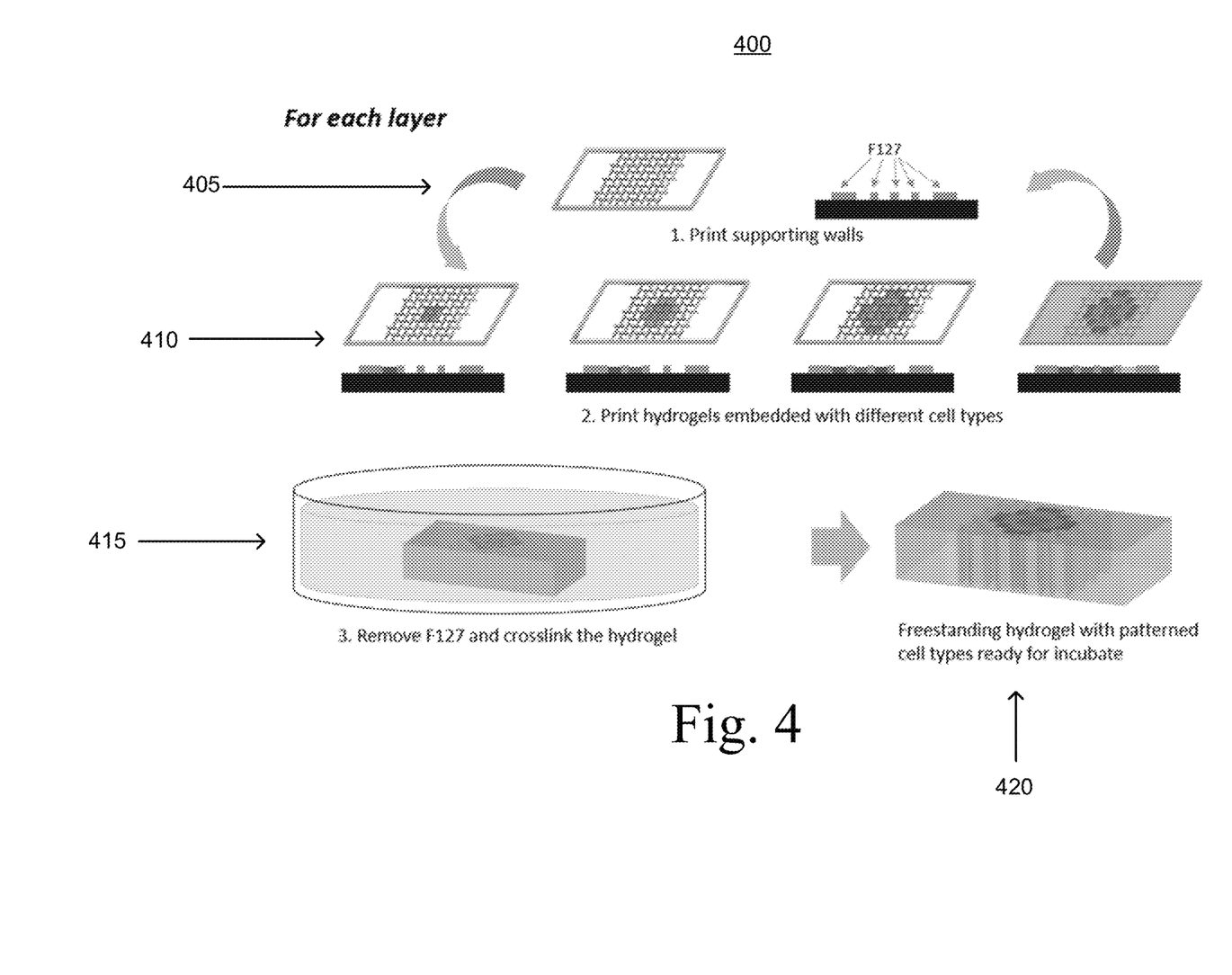
FIG. 4 depicts a method of manufacturing a system for growing a cell culture, according to an exemplary embodiment of the present invention.

After manufacturing, the cell-laden scaffold can be connected to a positioning system as shown in FIG. 2a. As shown in FIGS. 2b-c, the cycling of the scaffold between one or more expanded and contracted states can exhibit a quasi-static control pattern (FIG. 2b), a cyclic dynamic control pattern (FIG. 2c), or many other patterns.

In an exemplary quasi-static control pattern, the number of cells in the scaffold can be obtained through microscopic imaging at predetermined time intervals, e.g., every 24 hours. Using this count, the cell density change during the next time interval can be predicted based on modeling. The position of the second member 225 can be adjusted so a small increment will be given to the distance between the first member 220 and the second member 225. This essentially stretches the scaffold in the x direction. Because of its auxeticity, the overall volume of the scaffold increases, keeping cell density at a favorable level.

In an exemplary cyclic dynamic control pattern, the baseline position of the second member can increase each time interval, e.g., 24-hour period, as in the quasi-static control pattern. Between adjustments at each new time interval, however, the second member can continue a cyclic movement within a small range of Δx. The scaffold will continuously experience stretching and compressing, alternatively, which will facilitate microfluidic circulation throughout the scaffold.

Various embodiments of the present invention employing auxetic scaffolds provide greatly improved cell growth and/or cell survival as compared to conventional systems employing non-auxetic scaffolds. FIG. 5 provides microscopic images showing higher cell numbers over time (indicating greater cell survival rates) in systems employing auxetic scaffolds as compared to a conventional system employing a non-auxetic scaffold.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office, other organizations, and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the disclosed technology is defined by the claims appended hereto.

The invention claimed is:

1. A system for growing a cell culture comprising:
   an auxetic scaffold substrate comprising scaffold units, at least a portion of the scaffold units configured to transition between a contracted state and an expanded state and comprising:
      an interior void having a contracted volume and an expanded volume;
      a fluid inlet comprising a one-directional valve configured to enable the scaffold unit to receive a portion of a fluid into the interior void; and
      a fluid outlet comprising a one-directional valve configured to enable the scaffold unit to expel a portion of the fluid from the interior void;
   wherein the interior void has the contracted volume in the contracted state and the expanded volume in the expanded state, the expanded volume being greater than the contracted volume; and
   wherein each of the at least a portion of the scaffold units is further configured to:
      receive the portion of the fluid into the interior void when the unit transitions from the contracted state to the expanded state; and
      expel the portion of the fluid from the interior void when the unit transitions from the expanded state to the contracted state.

2. The system of claim 1, wherein the at least a portion of the scaffold units comprise all of the scaffold units of the auxetic scaffold substrate; and
   wherein the portion of the fluid received by a scaffold unit is substantially the same as the portion of the fluid expelled by the scaffold unit.

3. The system of claim 1, wherein each of the at least a portion of the scaffold units further comprise living cells; and
wherein the auxetic scaffold substrate further comprises a cell-laden hydrogel.

4. The system of claim 3, wherein the cell-laden hydrogel comprises mammalian stem cells.

5. The system of claim 1 further comprising a growth factor solution coated upon the auxetic scaffold substrate.

6. The system of claim 5, wherein the growth factor solution is selected from the group consisting of collagen, basic fibroblast growth factor, and epidermal growth factor.

7. The system of claim 1, wherein the fluid comprises one or more materials selected from the group consisting of amino acids, salts, sugars, and vitamins.

8. The system of claim 1 further comprising:
living cells provided in the at least a portion of the scaffold units;
a first member coupled to a first side of the auxetic scaffold substrate; and
a second member coupled to a second side of the auxetic scaffold substrate;
wherein the second member is configured to move between a contracted position and an expanded position;
wherein each of the at least a portion of the scaffold units is in the contracted state when the second member is in the contracted position; and
wherein each of the at least a portion of the scaffold units is in the expanded state when the second member is in the expanded position.

9. The system of claim 8 further comprising a controller configured to cycle the second member between the contracted position and the expanded position.

10. The system of claim 9, wherein the controller is further configured to, based on a parameter associated with the auxetic scaffold substrate, adjust at least one of:
at least one of the contracted position and the expanded position of the second member; and
a frequency at which the location of the second member is cycled between the contracted position and the expanded position.

11. The system of claim 10, wherein the parameter is indicative of at least one of a current cell-density of the living cells and a current growth rate of the living cells.

12. The system of claim 2, wherein the auxetic scaffold substrate is multi-layered and manufactured using a three-dimensional bioplotter.

13. A method of facilitating cell growth comprising:
providing living cells in the at least a portion of the scaffold units of the auxetic scaffold substrate of claim 1; and
providing the living cells with the fluid comprising one or more materials selected from the group consisting of amino acids, salts, sugars, and vitamins.

14. The method of claim 13, wherein the at least a portion of the scaffold units comprise all of the scaffold units of auxetic scaffold substrate; and
wherein the portion of the fluid received by a scaffold unit is substantially the same as the portion of the fluid expelled by the scaffold unit.

15. The method of claim 13 further comprising:
moving a second member coupled to a second side of the auxetic scaffold substrate between a contracted position and an expanded position;
wherein a first member is coupled to a first side of the auxetic scaffold substrate;
wherein each of the at least a portion of the scaffold units is in the contracted state when the second member is in the contracted position; and
wherein each of the at least a portion of the scaffold units is in the expanded state when the second member is in the expanded position.

16. The method of claim 15 further comprising moving the second member at a first frequency adjustable based on a parameter associated with the auxetic scaffold substrate.

17. The method of claim 16, wherein the parameter is indicative of at least one of a current cell-density of the living cells and a current growth rate of the living cells.

18. An auxetic system comprising:
scaffold units, each scaffold unit defining an interior void in fluidic communication with a fluid inlet and a fluid outlet; and
one or more living cells in one or more scaffold units;
wherein each scaffold unit is configured to transition between a contracted state in which the interior void has a contracted volume, and an expanded state in which the interior void has an expanded volume greater than the contracted volume;
wherein when the scaffold unit transitions from the contracted state to the expanded state, the fluid inlet is configured to permit one-way flow of the fluid into the interior void from outside the scaffold unit; and
wherein when the scaffold unit transitions from the expanded state to the contracted state, the fluid outlet is configured to permit one-way flow of the fluid out of the interior void to outside the scaffold unit.

19. The auxetic system of claim 18 further comprising:
a cell-laden hydrogel; and
a growth factor solution.

* * * * *